United States Patent [19]

Dall et al.

[11] 4,269,180

[45] May 26, 1981

[54] BONE FASTENER FOR THE GREATER TROCHANTER

[76] Inventors: Desmond M. Dall, 108 Medical Centre, Heerengracht, Cape Town, Cape Province; Anthony W. Miles, 15 E. Light Way, Kirstenhof, Cape Province, both of South Africa

[21] Appl. No.: 21,858

[22] Filed: Mar. 19, 1979

[30] Foreign Application Priority Data

Mar. 30, 1978 [GB] United Kingdom .............. 12365/78

[51] Int. Cl.³ .............................................. A61F 5/04
[52] U.S. Cl. ................................. 128/92 B; 128/92 D
[58] Field of Search ............... 128/92 B, 92 D, 92 G, 128/92 BA

[56] References Cited

U.S. PATENT DOCUMENTS

| 583,455 | 6/1897 | Bush | 128/92 D |
| 2,501,978 | 3/1950 | Wichman | 128/92 D |
| 3,824,995 | 7/1974 | Getscher et al. | 128/92 B |
| 3,997,138 | 12/1976 | Crock et al. | 128/92 B X |
| 4,120,298 | 10/1978 | Fixel | 128/92 B X |
| 4,146,022 | 3/1979 | Johnson et al. | 128/92 B |

*Primary Examiner*—Clifford D. Crowder
*Attorney, Agent, or Firm*—Ladas & Parry

[57] ABSTRACT

An implant of H shape for use in bone surgery, specifically in re-attaching the greater trochanter after osteotomy. The cross-bar (28) of the H forms a bridge and has two longitudinal holes (24) in it for receiving a tying cable (22). At each end of each limb (32, 36) of the H there is a tooth (34, 38) which is either impaled in, or fits around, the trochanter or other bone. The limbs can be straight in the region of the bridge or can be markedly curved. The teeth all lie on the same side of the structure constituted by the limbs and bridge, and, where the limbs are curved, lie on the inside of the curve.

12 Claims, 15 Drawing Figures

BONE FASTENER FOR THE GREATER TROCHANTER

This invention relates to an implant for use in bone surgery and to an assembly including the implant.

In many reconstructive procedures of the hip, osteotomy of the greater trochanter is employed as an approach to the joint. Sound re-attachment of the greater trochanter after osteotomy is important in obtaining re-union with the main shaft of the femur to provide good functional results from hip operations. The re-attachment system for the greater trochanter must ensure rigid immobilisation of the trochanter across the osteotomy site and allow early post-operative ambulation while bone union is in progress.

Existing methods of re-attachment of the greater trochanter include the use of U-bolts, bolts and clamps, and plates and screws. In addition there is a widely used method in which mono-filament wires are tied around the trochanter to secure it in place. Failure of the wiring system due to fracture or loosening has been reported. Good apposition of the greater trochanter is sometimes compromised during the final tensioning and tying of the wires, and this may result in a less than optimal functional result. Removal of the wires, should they fracture and migrate, is sometimes required and is technically quite difficult. There is thus considerable scope for improvement of existing systems and techniques.

According to the present invention there is provided an implant for use in bone surgery, the implant comprising a base structure including a pair of limbs joined by a bridge, a plurality of teeth protruding from the base structure, all the teeth lying on the same side of the base structure, and a hole in the base structure for receiving a cable.

In a preferred embodiment the base structure is H-shaped, the bridge constituting the cross-bar of the H and there being a tooth at each end of each limb.

Embodiments of the invention will now be described, by way of example, with reference to the accompanying drawings, in which:

FIG. 15 illustrates an implant with two bridges.

Figure 1:
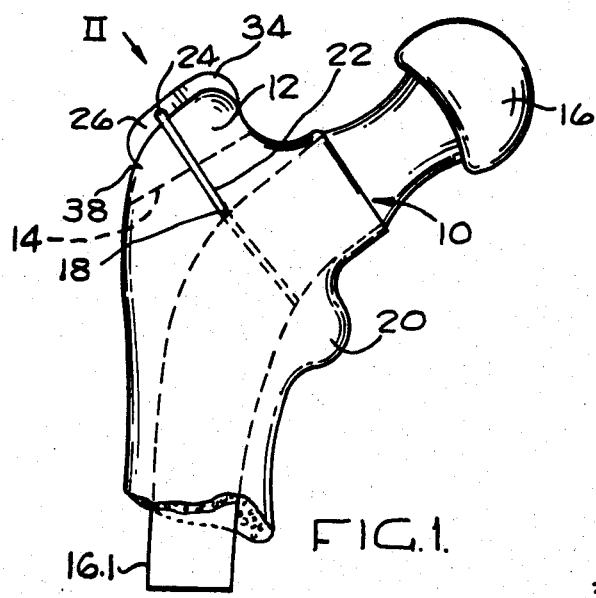
FIG. 1 illustrates part of a femur after an operation.

In a hip joint replacement operation, the greater trochanter 12 is severed from the remainder of the femur at a zone 14 and the femoral head is severed from the remainder of the femur at a zone 10. Removal of the trochanter 12 enables the muscle secured thereto to be folded back and permit greater exposure of, and access to, the operation site. The medullary cavity of the femur is then reamed and prepared to receive the stem 16.1 of a prosthetic head 16 which replaces the original head.

In accordance with a procedure devised by the Applicants, a hole 18 is drilled through the femur, the hole intersecting the medullary cavity. A cable 22 is passed through the hole 18 and a surgical instrument used to pull a loop of cable into the medullary cavity. The tapered stem 16.1 of the prosthetic head 16 is entered in the medullary cavity and passed through the loop of cable 22. Thus the cable enters the medullary cavity, extends around about three quarters of the periphery of the stem 16.1 and exits from the cavity. The stem 16.1 is subsequently cemented into the cavity.

Figure 2:
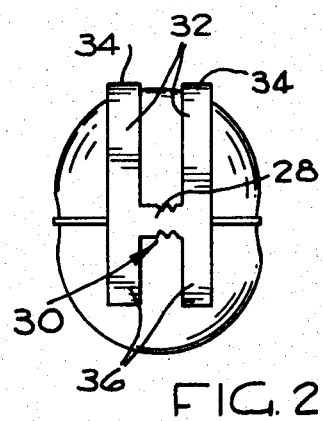
FIG. 2 is a schematic representation of the greater trochanter, seen in the direction of arrow II.
Figure 3:
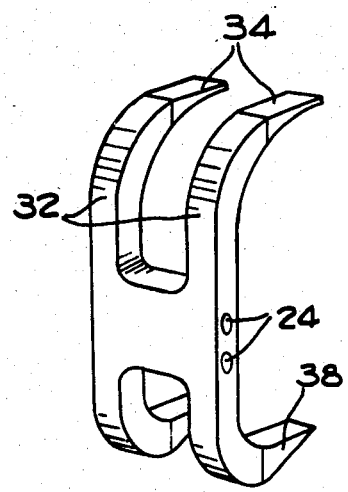
FIG. 3 is a three-dimensional view of an implant for use in locating a trochanter.
Figure 4:
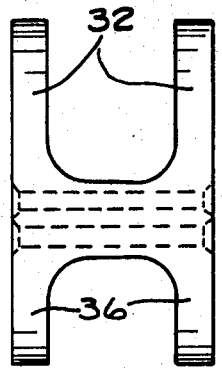
FIG. 4 is a front elevation of the implant of FIG. 3.
Figure 5:
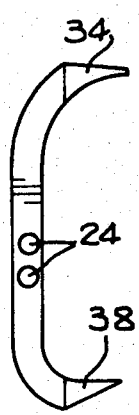
FIG. 5 is a side view of the implant.

The two ends of the cable 22 are fed in opposite directions through holes 24 in a bridge 28 of an implant 26. The bridge 28 is then crimped onto the cable in order to fix the cable in position. For example it can be crimped as shown at 30 to form two vee-grooves (FIG. 2). Before crimping, the cable is tensioned using conventional wire tighteners and after crimping excess cable is snipped off close to the implant. If desired a single hole 24 can be provided and the ends of the cable pushed in from opposite sides until they abut.

While the cable 22 can contact the stem 16.1 once it has been pulled tight, it can also happen that it is embedded in the cement out of contact with the stem 16.1.

The cable 22 consists of a multi-filament cable, which may be coated with a suitable plastics material. The strands of the cable may be of stainless steel or other suitable material which will not corrode and is biologically compatible in the body.

The provision of the multi-filament cable instead of a mono-filament wire can significantly reduce the risk of fracture due to damage or fatigue. The resistance to damage is particularly important in reducing the breakage of the cable in a region of crimping and elsewhere where kinking in monofilament wire results in breakage.

The implant 26, like the cable, is made of stainless steel or other suitable material. It is also non-corrosive and biologically compatible in the body.

The implant has two curved limbs 32 which extend upwardly from the bridge 28. The limbs 32 each terminate in a tooth 34 which fits over the upper part of the greater trochanter 12 as shown in FIG. 1 or is shaped to penetrate into the trochanter. On the opposite side of the bridge 28, the implant has limbs 36 which are parallel to the limbs 32 and which end in teeth 38. The teeth 38 penetrate the greater trochanter and firmly secure the implant in position. Thus, the implant is held against movement around the trochanter by the limbs 32 and 36 and the teeth 34 and 38 and is pressed firmly against the greater trochanter by the tensioned cable 22. The bridge 28 and limbs 32, 36 form a base structure, and the teeth 34 and 38 all lie on the same side of the base structure.

The teeth can be forced into the trochanter or can be inserted into pre-drilled holes.

The provision for crimping and therefore rapid fixation of the cable allows operating time to be reduced and provides for a rigid fixation of the trochanter. Furthermore, it can be simpler to use than existing methods.

In some cases, it may be desirable to use more than one cable 22, in which case two bridges 28.1, 28.2 (FIG. 15) similar to the bridge 28 may be provided.

In practice, the cable, whether coated or not, will normally have its strands made of the same material as the implant to eliminate electrolytic action between the cable and the implant in the body. Furthermore, while the height of the implant may be adjusted to suit different conditions, the height will probably be in the region of 3 cm. Also, the location of the bridge 28 in relation to the proportionate lengths of the limbs 32 and 34 may be varied.

Figure 8:
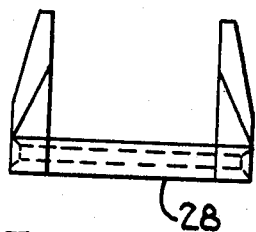
FIGS. 6, 7 and 8 are respectively a side view, an elevation a top plan view of a further implant.
Figure 7:
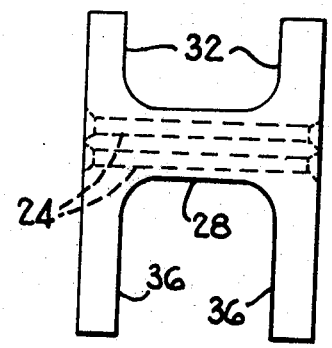
Figure 6:
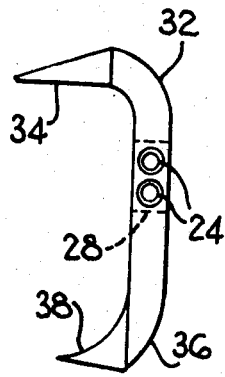
Figure 14:
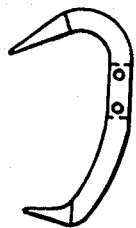
FIGS. 9 to 14 are side views, to a smaller scale, of alternative implants 1
Figure 13:
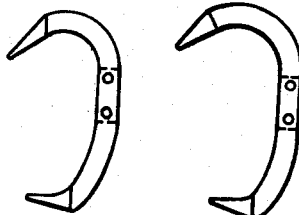
Figure 12:
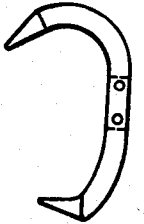
Figure 11:
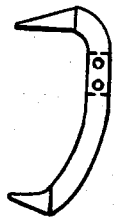
Figure 10:
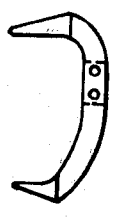
Figure 9:
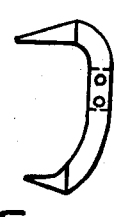

The implants shown in FIGS. 6 to 8 and each of FIGS. 9 to 14 have bridges 28 with holes 24 therein, limbs 32 and 36, and teeth 34 and 38. The various implants differ from one another insofar as their shape is concerned, the limbs of FIG. 9 etc being more curved than the limbs of the earlier Figures. The implants of FIGS. 6 to 8, and 9 to 11 are designed so that all their teeth penetrate the trochanter. The forms of FIGS. 12 to 14 are the same as that shown in FIGS. 1 to 5 in that the teeth 34 are intended to fit around the trochanter and the teeth 38 are intended to embed in the trochanter.

The implants described and illustrated are specifically intended for use in fixing the greater trochanter to the shaft of the femur after a hip-joint operation. In this form the implant height mentioned, 3 cm, is usually sufficient. Where the implant is used to treat, for example, a bone fracture it can be of greater height, say up to 7 cm.

The base structure of a further form of implant according to the invention, which has not been illustrated, is in the form of a capital A. There is a single tooth at the apex of the A and a further tooth at the free end of each limb. The hole or holes pass longitudinally through the cross-bar of the A and through the two limbs, or through the two limbs.

We claim:

1. An implant for use in bone surgery, the implant comprising a base structure including a pair of limbs joined by a bridge, the bridge being bounded by a front face, a rear face and edge faces, a plurality of teeth protruding from the base structure, all the teeth lying on the same side of the base structure, and a hole in the base structure for receiving a cable, the hole being elongate in form, extending lengthways through the bridge, and being open at each end.

2. An implant as claimed in claim 1, wherein two holes are provided, the holes being parallel to one another.

3. An implant as claimed in claim 1, wherein each limb includes a straight, central portion and curved end portions, the end portions being curved in the same direction and the teeth being on the insides of the curves.

4. An implant as claimed in claim 3, wherein the radius of curvature of one end portion of each limb is greater than the radius of curvature of the other end portion of each limb.

5. An implant as claimed in claim 3, wherein there is a tooth at each end of each limb.

6. An implant as claimed in claim 1 wherein said teeth are wedge shaped.

7. An implant as claimed in claim 1, 2 or 3, wherein said base structure is H-shaped, said bridge constituting the cross-bar of the H.

8. An implant as claimed in claim 1, and including a further bridge spaced from, and parallel to, the first mentioned bridge, there being an elongate hole extending lengthways through the further bridge, the hole being open at each end.

9. An implant as claimed in claim 8 in which two holes are provided in each bridge, the two holes in each bridge being parallel to one another.

10. A method of re-securing the greater trochanter which comprises drilling a hole through the femur, passing a multi-filament cable through the hole in the femur, placing against the trochanter an implant comprising a base structure including a pair of limbs joined by a bridge, the bridge being bounded by a front face, a rear face and edge faces, a plurality of teeth protruding from the base structure, all the teeth lying on the same side of the base structure, and a hole in the base structure for receiving the cable, the hole being elongate in form, extending lengthways through the bridge, and being open at each end, feeding the ends of the cable into said hole from opposite ends thereof in such manner as to pull the implant against the trochanter so that the teeth are embedded therein, and crimping said bridge to secure said cable to the implant.

11. A method of re-securing the greater trochanter which comprises drilling a hole through the femur, passing a multifilament cable through the hole in the femur, placing against the trochanter an implant comprising a base structure including a pair of limbs joined by a bridge, the bridge being bounded by a front face, a rear face and edge faces, a plurality of teeth protruding from the base structure, all the teeth lying on the same side of the base structure, and two holes in the base structure for receiving the cable, the holes being elongate in form, extending lengthways through the bridge, and being open at each end, feeding the ends of the cable one into each of said holes from opposite ends thereof, pulling the cable tight to urge the implant against the trochanter so that the teeth are embedded therein, and crimping said bridge to secure said cable to the implant.

12. A method as claimed in claim 11, in which two holes are drilled in the femur and two cables are fed through these holes, and in which the implant has two bridges each with two holes therein, the ends of one cable being fed through the holes in one bridge of the implant in opposite directions and the ends of the other cable being fed through the holes in the other bridge of the implant in opposite directions, both cables being pulled tight by opposing forces exerted on their ends, the bridges subsequently being crimped and the excess lengths of the two cables being cut off.

* * * * *

UNITED STATES PATENT AND TRADEMARK OFFICE
CERTIFICATE OF CORRECTION

PATENT NO. : 4,269,180

DATED : May 26, 1981

INVENTOR(S) : Desmond Meiring DALL et al

It is certified that error appears in the above—identified patent and that said Letters Patent is hereby corrected as shown below:

The drawings should include the Figure 15 shown on the attached sheet.

UNITED STATES PATENT AND TRADEMARK OFFICE
CERTIFICATE OF CORRECTION

PATENT NO. : 4,269,180

DATED : May 26, 1981

INVENTOR(S) : Desmond Meiring DALL et al

Page 2 of 2

It is certified that error appears in the above—identified patent and that said Letters Patent is hereby corrected as shown below:

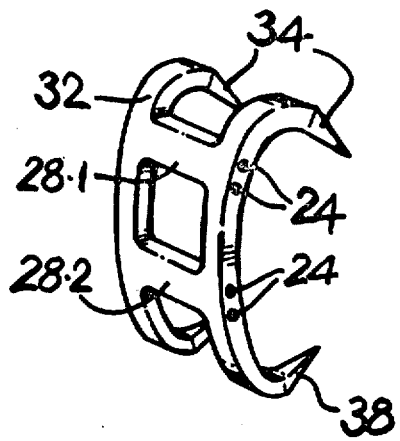

FIG 15

Signed and Sealed this

Sixteenth Day of February 1982

[SEAL]

Attest:

Attesting Officer

GERALD J. MOSSINGHOFF

Commissioner of Patents and Trademarks